United States Patent [19]
Liu et al.

[11] Patent Number: 5,635,716
[45] Date of Patent: Jun. 3, 1997

[54] METHOD FOR IDENTIFYING SURFACE ATOMS OF SOLID SAMPLE AND APPARATUS THEREFOR

[75] Inventors: Ziyuan Liu, Kawasaki; Tadataka Morishita, Kanagawa-ken, both of Japan

[73] Assignee: International Superconductivity Technology Center, Japan

[21] Appl. No.: 614,678

[22] Filed: Mar. 13, 1996

[30] Foreign Application Priority Data

Mar. 17, 1995 [JP] Japan ................................. 7-059184

[51] Int. Cl.$^6$ .................................................. H01J 37/26
[52] U.S. Cl. ............................ 250/310; 250/305; 378/44
[58] Field of Search ............................ 250/310, 306, 250/307, 305, 397–398; 378/44, 45, 46, 83, 86, 88, 90

[56] References Cited

U.S. PATENT DOCUMENTS

| | | | |
|---|---|---|---|
| 4,746,571 | 5/1988 | Kelly | 250/310 |
| 5,093,573 | 3/1992 | Mikoshiba et al. | 250/310 |
| 5,369,275 | 11/1994 | Usui et al. | 250/310 |

Primary Examiner—Jack I. Berman
Assistant Examiner—Kiet T. Nguyen
Attorney, Agent, or Firm—Lorusso & Loud

[57] ABSTRACT

The atoms constituting a surface of a solid sample are identified by first forming, on the surface, island-like deposits of a substance capable of generating fluorescent X-rays upon being energized by an electron beam. The deposits are then energized with the electron beam so that fluorescent X-rays are emitted therefrom and reflected on the surface. From the critical angle for total reflection of the fluorescent X-rays reflected on that portion of the surface of the sample on which no deposits are present, the atoms constituting the surface may be determined. An apparatus for carrying out the above method is also disclosed which is a modification of the conventional RHEED/TRAXS device.

5 Claims, 5 Drawing Sheets

METHOD FOR IDENTIFYING SURFACE ATOMS OF SOLID SAMPLE AND APPARATUS THEREFOR

BACKGROUND OF THE INVENTION

This invention relates to a method of determining the surface atomic layer of a solid sample by a reflection high energy electron diffraction (RHEED) method combined with (TRAXS) total reflection angle X-ray spectroscopy.

In the conventional RHEED method, the characteristic X-rays emitted from a surface of a sample when an electron beam is impinged thereon are detected to determine the elements constituting the surface of the sample. One problem of the RHEED method is a low measurement sensitivity attributed to the low intensity of the characteristic X-rays.

JP-A-60-82840 discloses RHEED/TRAXS analysis method in which, as shown in FIG. 9, the characteristic X-rays (fluorescent X-rays) Cx emitted from a surface of a sample 15 excited by an electron beam Ei with an incident angle α from an electron gun 16 are detected by a detector 17 at the total reflection angle β. This method is advantageous because of a high detection sensitivity but has a problem because the X-ray penetration depth is not sufficiently small (30–50 Å) and because the analysis is unable to perform when the surface to be detected is not smooth.

More particularly, when the conventional RHEED/TRAXS analysis is adopted to, for example, a (100) plane of a perovskite crystal of $ABO_3$ in which the atomic layer containing the element A and the atomic layer containing the element B are alternately stacked, not only the outermost atomic layer but also the inner adjacent layer are simultaneously energized with the electron beam, so that it is impossible to identify the outermost atomic layer. In order to minimize the penetration depth as small as possible, therefore, it is necessary to set the incident angle α at about 0.1–1 radian. In this case, when the sample has a rough surface, it is impossible to obtain the critical angle for total reflection at positions as shown in FIG. 10.

SUMMARY OF THE INVENTION

It is, therefore, an object of the present invention to provide a RHEED/TRAXS analysis method which can minimize the X-ray penetration depth and which can identify the outermost surface atomic layer of a solid sample with a high detection sensitivity.

Another object of the present invention is to provide a method which can determine the surface atomic layer of a solid sample having a roughed surface.

In accomplishing the foregoing objects, there is provided in accordance with the present invention a method of determining the atoms constituting a surface of a solid sample, comprising the steps of:

forming, on a surface of said sample, island-like deposits of a substance capable of generating fluorescent X-rays upon being energized by an electron beam, such that said island-like deposits are surrounded by a non-coated surface of said sample;

energizing said deposits with the electron beam so that fluorescent X-rays are emitted therefrom and reflected on said non-coated surface; and measuring the critical angle for total reflection of the fluorescent X-rays reflected on said non-coated surface of said sample.

In the present invention, the electron beam is impinged on the island-like deposits rather than on the sample. The island-like deposits serve to function as an X-ray source. Thus, the fluorescent X-rays emitted from the island-like deposits are impinged on a surface of the sample. The critical angle for total reflection of the fluorescent X-rays reflected on the surface is measured. By this expedient, the effective penetration depth of the evanescent wave is in the range of about 10–20 Å, so that the outermost atomic layer can be identified with high resolution, irrespective of the incident angle of the electron beam. Further, since the X-ray source is small in size and is present adjacent to the surface to be measured, the surface roughness of the sample does not adversely affect the identification of the surface atomic layer thereof.

In another aspect, the present invention provides a device for determining the surface atomic layer of a solid sample, comprising:

a vessel defining an airtight chamber therewithin;

evacuation means for maintaining said chamber in a vacuum state;

a holder disposed in said chamber for securing said sample at a predetermined orientation;

heater means for heating said sample, so that when a substance capable of generating fluorescent X-rays upon being energized by an electron beam is placed in said chamber and heated under vacuum, islands-like deposits may be formed on a surface of said sample with each deposit being surrounded by non-coated surface of said sample;

an electron beam gun for impinging electron beams either on said sample placed in said chamber or on said islands-like deposits on said sample; and means for measuring the critical angle for total reflection of the fluorescent X-rays reflected on said non-coated surface.

BRIEF DESCRIPTION OF THE DRAWINGS

Other objects, features and advantages of the present invention will become apparent from the detailed description of the preferred embodiments of the invention which follows, when considered in the light of the accompanying drawings, in which.

DETAILED DESCRIPTION OF THE PREFERRED EMBODIMENTS OF THE INVENTION

Figure 1:
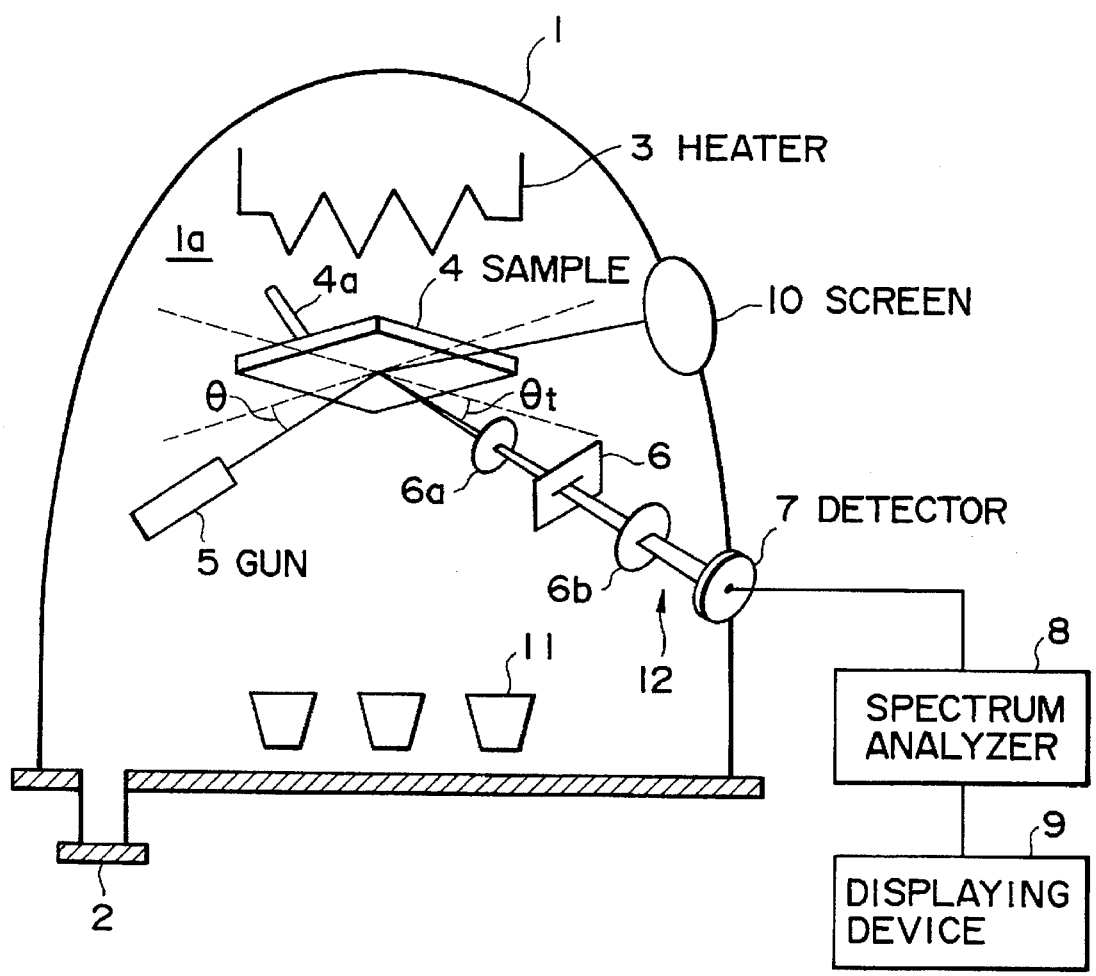
FIG. 1 is a schematic illustration of a surface element detecting device according to the present invention.
Figure 2:
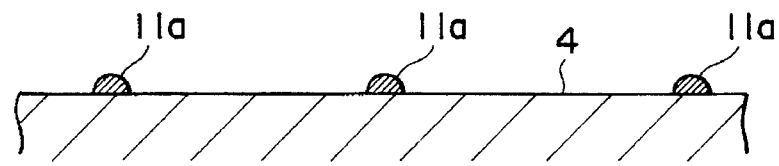
FIG. 2 is a sectional view schematically illustrating island-like deposits on a sample to be measured.

Referring now to FIG. 1, designated as 1 is a vessel defining therewithin an airtight chamber 1a and having an evacuation port connected to a vacuum pump (not shown) for maintaining the chamber 1a in a vacuum state. Disposed in the chamber 1a is a sample holder 4a for securing a sample 4 to be measured at a predetermined orientation. Heater means 3 is disposed in the chamber 1a for heating the sample 4. Designated as 11 is a substance capable of generating fluorescent X-rays upon being energized by an electron beam.

Disposed also in the chamber 1a is an electron gun which may be a primary electron beam source used in the conventional RHEED. The electron gun 5 is used for forming island-like deposits 11a of the substance 11 as well as for exciting the island-like deposits 11a on the sample 4 so as to emit fluorescent X-rays therefrom. The island state of the deposits 11a formed on the sample 4 is confirmed by a RHEED screen 10.

Designated generally as 12 is means for measuring the critical angle for total reflection of the fluorescent X-rays reflected on a surface of the sample 4. The measuring means 12 may be conventional one used in TRAXS and includes a Si(Li) energy dispersive X-ray detector 7 arranged to receive the exiting X-rays through a slit 6 and Be windows 6a and 6b, a spectrum analyzer 8 and memorizing and display means 9. The orientation angle $\theta_r$ of the detector 7 relative to the surface of the sample 4 may be changed around the critical angle $\theta_c$ for total reflection.

Figure 4:
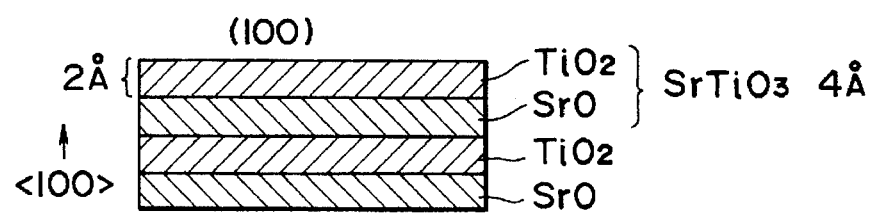
FIG. 4 is a schematic illustration of the atomic layer structure of $SrTiO_3$.

With the foregoing structure of the surface atomic layer identification device, when the substance 11 is excited with the electron gun 5, while heating the sample 4 with the heater 3 at, for example, 200°–300° C. and while maintaining the chamber 1a in vacuum state, the substance 11 deposits on a surface of the sample 4 secured in the vacuum chamber 1a by the holder 4a, thereby to form, as shown in FIG. 4, island-like deposits 11a randomly distributed on the sample 4 and each surrounded by non-coated surface of the sample 4. The diameter of each of the deposits 11a is preferably 5–1,000 mm, more preferably 10–100 nm.

Figure 3:
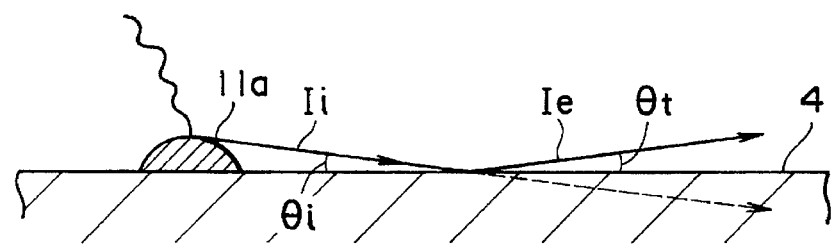
FIG. 3 is a sectional view, similar to FIG. 2, showing the function of the island-like deposits.

The electron beam is then impinged upon the island-like deposits 11a so that the fluorescent X-rays are emitted therefrom in all directions around the islands 11a. In this case, the island state of the deposits 11a may be confirmed by a pattern formed on the RHEED screen 10. As shown in FIG. 3, the incoming X-rays $I_i$ impinge on the surface of the sample 4 and encounter the total reflection on the surface when the incident angle $\theta_i$ is smaller than the critical angle $\theta_c$. Since the critical angle $\theta_c$ for total reflection is given by:

$$\theta_c = 1.14\sqrt{\rho}/E$$

wherein $\rho$ is the density (g/cm$^3$) of the surface of the sample 4 and E is the energy (KeV) of the X-rays, the surface atomic layer can be identified by measuring the critical angle $\theta_c$ for total reflection. Thus, the intensity of the exiting X-rays $I_e$ at exiting angle $\theta_r$ is detected by the detector 7 (FIG. 1) while changing the angle of the direction of the detector 7 relative to the sample 4. The outputs from the detector 7 are analyzed in the spectrum analyzer 8 and the results are memorized and displayed in the device 9, whereupon the critical angle for total reflection $\theta_c$ is determined.

The following examples will further illustrate the present invention.

EXAMPLE 1

Figure 5:
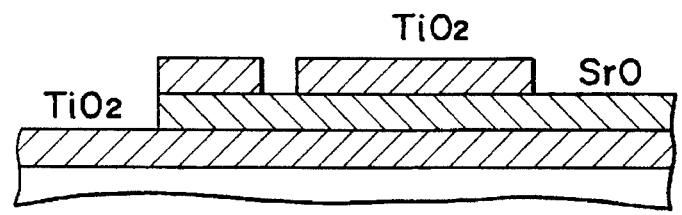
FIG. 5 is a schematic illustration of microscopic surface structure of $SrTiO_3$.

As shown in FIG. 4, SrTiO$_3$ (001) perovskite single crystal has a layer structure in which TiO$_2$ (2 Å) and SrO (2 Å) atomic layers are alternately stacked. It is known that the surface layer depends on the surface treatment. For example, a SrTiO$_3$ surface annealed shows two kinds of termination layers as shown in FIG. 5.

Figure 6:
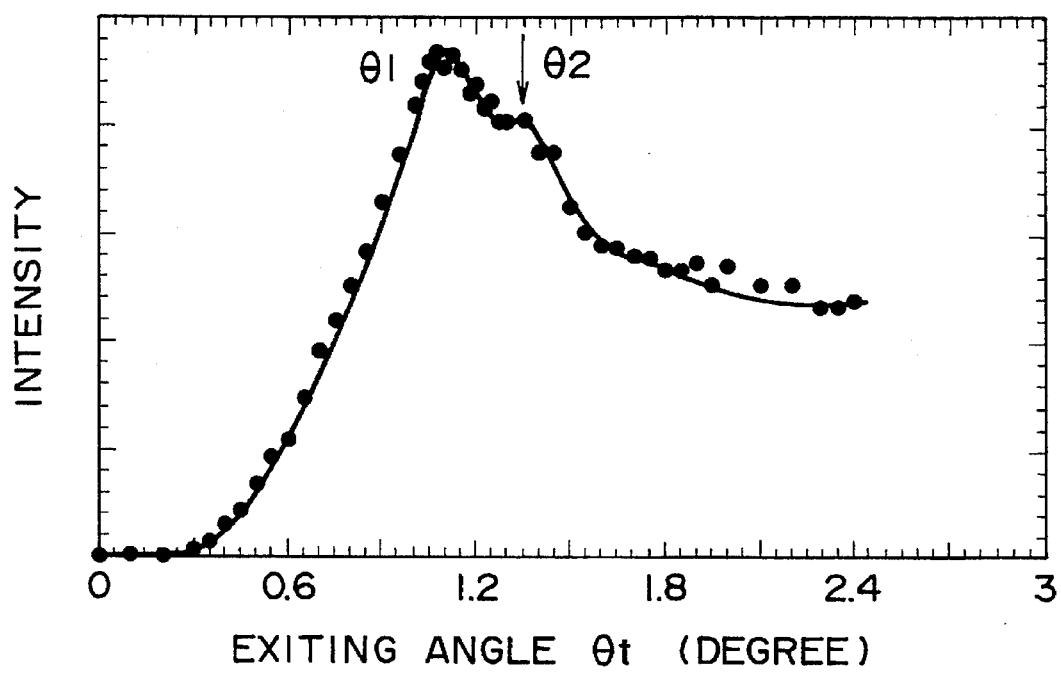
FIG. 6 shows the exit angle dependency of an exiting X-ray (Au $M_α$ X-ray) obtained in the surface layer identification of $SrTiO_3$ in Example 1.

Thus, a SrTiO$_3$ sample annealed at 1,000° C. for 10 hours in 1 atm oxygen was measured for the identification of the surface atomic layer by the method according to the present invention. The sample was set in a vacuum chamber of RHEED-TRAXS as shown in FIG. 1 and Au deposits were formed in situ on a surface of the sample by electron beam deposition using the primary electron beam of the RHEED. The RHEED and high resolution scanning electron microscopy were used to confirm the island state of the Au deposits. A Si(Li) energy-dispersive X-ray detector with a resolution of 165 eV, which located at 45° from the direction of the primary electron beam, was combined with the vacuum chamber through a slit and Be windows. The slit with a 0.2 mm separation insured an angular resolution of 0.05°. In order to observe intensity variation of an exiting X-ray (Au M$_\alpha$ X-ray) as a function of the exit angle $\theta_r$, the detector was moved on a circle centered at the sample surface in the vertical plane within 0°–3°. The results are shown in FIG. 6. Two peaks $\theta_1$ and $\theta_2$ representing the critical angles for total reflection were observed.

Table 1 shows the values of $\theta_1$ and $\theta_2$ observed from FIG. 6 and calculated critical angle $\theta_c$ for Au M$_\alpha$ X-ray (E=2.12 KeV). Also shown in Table 1 are values of $\rho_{layer}$ calculated for TiO$_2$ and SrO layers, and $\rho_{unit}$ for bulk SrTiO$_3$. As will be appreciated from Table 1, values of $\theta_1$ and $\theta_2$ are much closer to the calculated $\theta_c$ values based on $\rho_{layer}$ for TiO$_2$ and SrO layers than that based on $\rho_{unit}$ for bulk SrTiO$_3$. Namely, the results observed by the present method identified that the annealed SrTiO$_3$ surface was mainly terminated with TiO$_2$ plane (giving the peak $\theta_1$) with a small portion covered by SrO plane (giving the peak $\theta_2$).

TABLE 1

|  | $\theta_c$ (degree) | $\rho$ (g/cm$^3$) |
| --- | --- | --- |
| Found |  |  |
| $\theta_1$ | 1.10 |  |
| $\theta_2$ | 1.34 |  |
| Calculated |  |  |
| TiO$_2$ | 1.13 | 4.46 ($\rho_{layer}$) |
| SrO | 1.29 | 5.80 ($\rho_{layer}$) |
| SrTiO$_3$ | 1.21 | 5.13 ($\rho_{unit}$) |

EXAMPLE 2

Figure 7:
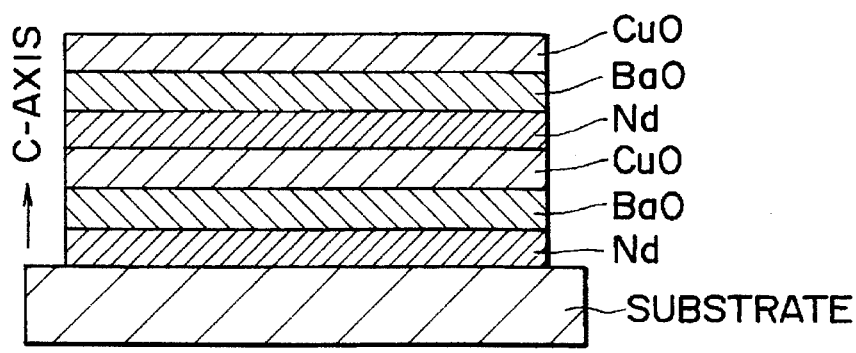
FIG. 7 is a schematic illustration of microscopic surface structure of $NdBa_2Cu_3O_x$.

An NBCO (NdBa$_2$Cu$_3$O$_x$ (6<x≦7)) film having a thickness of 100 nm was laminated on a SrTiO$_3$ substrate by a laser ablation process. The structure of the laminate is schematically shown in FIG. 7. The surface atomic layer of the NBCO film was identified by a method similar to that of Example 1. Ag was used to form island-like deposits. The results are shown in FIG. 8 and Table 2.

Figure 8:
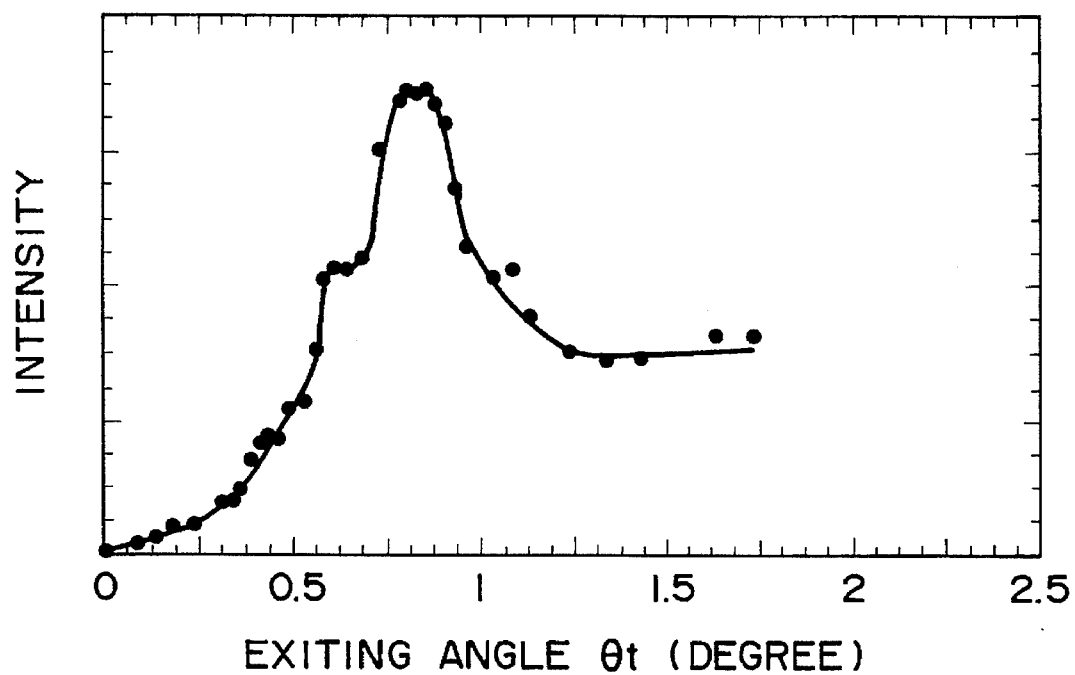
FIG. 8 shows the exit angle dependency of an exiting X-ray (Ag $L_α$ X-ray) obtained in the surface layer identification of $NdBa_2Cu_3O_x$ in Example 2.
Figure 9:
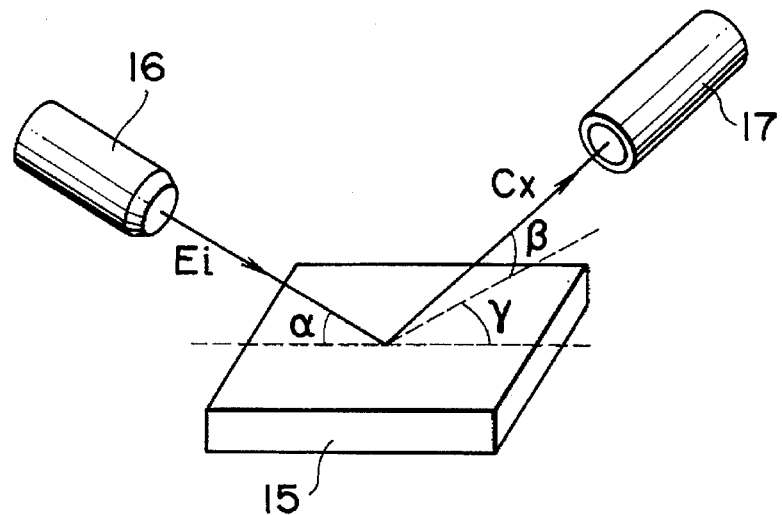
FIG. 9 is a schematic illustration of the known RHEED/TRAXS.
Figure 10:
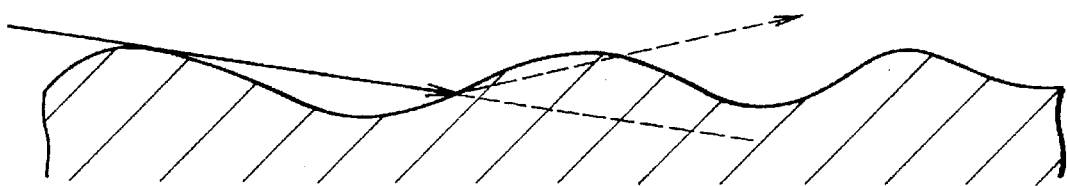
FIG. 10 is a schematic illustration of RHEED/TRAXS method applied to the measurement of a roughed surface.

FIG. 8 shows the intensity variation of Ag L$_\alpha$ X-ray (E=2.986 KeV) emitted from the Ag adlayer deposited on the NBCO film surface with the exit angle $\theta_r$. Table 2 shows the values of $\theta_1$ observed from FIG. 8 and calculated critical angle $\theta_c$ values. Also shown in Table 1 are values of $\rho_{layer}$ calculated for respective atomic layers, and $\rho_{unit}$ for bulk NdBa$_2$Cu$_3$O$_x$. As will be appreciated from Table 2, the surface atomic layer of the NBCO film is CuO or Cu$_2$O. This result is in conformity with that obtained by atomic force microscope (AFM).

TABLE 2

|  | $\theta_c$ (degree) | $\rho$ (g/cm$^3$) |
| --- | --- | --- |
| Found |  |  |
| $\theta_1$ Calculated | 0.83 |  |
| Nd | 1.14 | 8.06 ($\rho_{layer}$) |
| BaO | 1.09 | 8.75 ($\rho_{layer}$) |
| CuO | 0.77 | 4.53 ($\rho_{layer}$) |
| Cu$_2$O | 0.91 | 5.44 ($\rho_{layer}$) |
| NdBa$_2$Cu$_3$O$_x$ | 0.99 | 6.70 ($\rho_{unit}$) |
| BaCuO$_2$ | 0.92 | 5.82 ($\rho_{unit}$) |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of determining atoms constituting a surface of a solid sample, comprising the steps of:

forming, on a surface of said sample, island deposits of a substance generating fluorescent X-rays upon being energized by an electron beam, such that said island deposits are surrounded by a non-coated surface of said sample;

energizing said deposits with the electron beam so that fluorescent X-rays are emitted therefrom and reflected on said non-coated surface; and measuring the critical angle for total reflection of the fluorescent X-rays reflected on said non-coated surface of said sample.

2. A method as claimed in claim 1, wherein said substance is gold, silver or copper.

3. A method as claimed in claim 1, wherein said deposits each has a diameter of 5–1,000 nm.

4. A device for determining a surface atomic layer of a solid sample, comprising:

a vessel defining an airtight chamber therewithin;

evacuation means for maintaining said chamber in a vacuum state;

a holder disposed in said chamber for securing said sample at a predetermined orientation;

heater means for heating said sample, so that when a substance generating fluorescent X-rays upon being energized by an electron beam is placed in said chamber and heated under vacuum, island deposits are formed on a surface of said sample with each deposit being surrounded by a non-coated surface of said sample;

an electron beam gun for impinging electron beams on said island deposits on said sample; and means for measuring the critical angle for total reflection of the fluorescent X-rays reflected on said non-coated surface.

5. A device as claimed in claim 4, further comprising means for detecting island state of said deposits.

* * * * *

UNITED STATES PATENT AND TRADEMARK OFFICE
CERTIFICATE OF CORRECTION

PATENT NO. : 5,635,716
DATED : June 3, 1997
INVENTOR(S) : LIU, et. al.

It is certified that error appears in the above-indentified patent and that said Letters Patent is hereby corrected as shown below:

Col. 3, line 37, "mm" should read --nm--.

Signed and Sealed this

Twenty-fifth Day of August, 1998

Attest:

BRUCE LEHMAN

*Attesting Officer*  *Commissioner of Patents and Trademarks*